(12) United States Patent
Turner et al.

(10) Patent No.: US 6,680,204 B1
(45) Date of Patent: Jan. 20, 2004

(54) POLYMER FOR BINDING AMINE CONTAINING LIGANDS AND USES THEREOF

(75) Inventors: Anthony P. F. Turner, North Crawley (GB); David C. Cullen, Cambridge (GB); Sergiy A. Piletsky, Cranfield (GB); Olena V. Piletska, Cranfield (GB); Uwe Schedler, Berlin (DE); David Weston, deceased, late of Aston Clinton (GB), by Ralph John Weston, legal representative

(73) Assignee: Cranfield University, Cranfield (GB)

( * ) Notice: Subject to any disclaimer, the term of this patent is extended or adjusted under 35 U.S.C. 154(b) by 0 days.

(21) Appl. No.: 09/926,368

(22) PCT Filed: Apr. 25, 2000

(86) PCT No.: PCT/GB00/01590

§ 371 (c)(1),
(2), (4) Date: Apr. 22, 2002

(87) PCT Pub. No.: WO01/06256

PCT Pub. Date: Jan. 25, 2001

(30) Foreign Application Priority Data

Apr. 22, 1999 (GB) .............................................. 9909245

(51) Int. Cl.$^7$ ............................................. G01N 33/543
(52) U.S. Cl. ........................ 436/111; 436/161; 436/172
(58) Field of Search .............................. 436/86–90, 111, 436/112, 164, 166, 172, 161, 531, 532

(56) References Cited

U.S. PATENT DOCUMENTS

| | | | |
|---|---|---|---|
| 4,177,038 A | 12/1979 | Biebricher et al. | |
| 4,250,267 A | 2/1981 | Hartdegen et al. | |
| 5,436,161 A | 7/1995 | Bergstroem et al. | |
| 5,981,734 A | * 11/1999 | Mirzabekov et al. | ...... 536/25.3 |
| 6,562,581 B2 | * 5/2003 | Law et al. | ..................... 435/14 |

FOREIGN PATENT DOCUMENTS

| | | |
|---|---|---|
| EP | 0 233 973 | 9/1987 |
| JP | 4-323209 | * 11/1992 |
| WO | WO 93/02115 | * 2/1993 |

OTHER PUBLICATIONS

I.H.S. Al–Deen et al, "Assay of picomole quantities of polyamines by high pressure ion–exchange chromatography" Proceedings of the B.P.S., Sep. 13th–15th 1978, p. 465P.*

B. Tamami et al, "Poly(vinyl pyridine) supported silver dichromates as versatile, mild and efficient oxidants for different organic compounds," Polymer, vol. 32, No. 14, pp 2666–2670 (1991).*

(List continued on next page.)

Primary Examiner—Jeffrey Snay

(74) Attorney, Agent, or Firm—Oblon, Spivak, McClelland, Maier & Neustadt, P.C.

(57) ABSTRACT

Reaction of a dialdehyde, particularly phthaldialdehyde (I), with R—Z where Z is a nucleophilic group (preferably SH) and R is polymerisable (e.g. allyl) gives a reactive thioacetal (V) which can react with an amine ligand L—$NH_2$ to produce an isoindole (IV) which may be fluorescent. At some stage, generally before interaction with L—$NH_2$, the R groups are polymerised, possibly leading to self-assembly of the polymer on a metal or SH-bearing surface. Such a coated surface is useful as a transducer in assays or as a binding medium e.g. for chromatography.

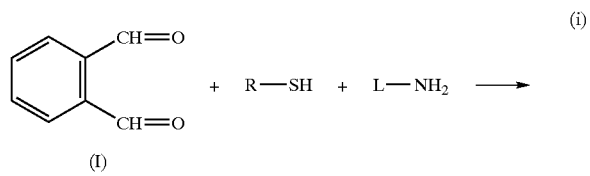

(i)

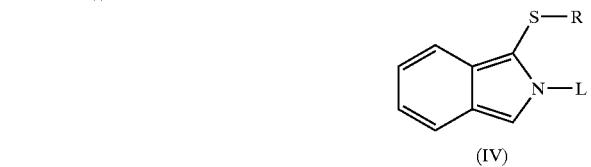

(ii)

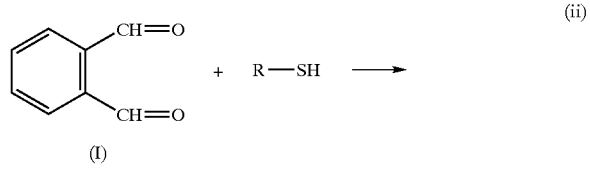

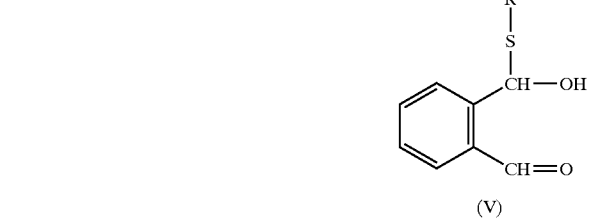

(iii)

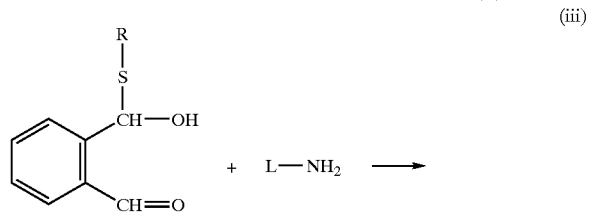

Thioacetal

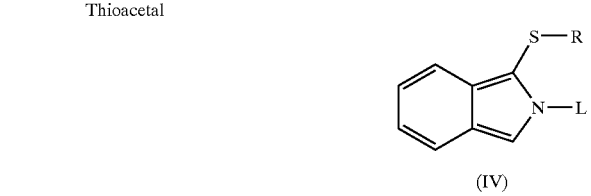

36 Claims, 5 Drawing Sheets

OTHER PUBLICATIONS

I. Molnar-Perl et al.: "Stability and characteristics of the o-phthaldialldehyde/3-mercaptopro Pionic acid and o-phthaldialdehyde/N-acetyl-1-cysteine reagents and their amino acid derivatives measured by high-performance liquid chromatography" Journal of Chromatography, vol. 835, No. 1–2, pp. 73–91 Mar. 12, 1999.

M. Aminuddin et al.: "Some aspects of spectrophotometric determination of aminoacids using o-phthalaldehyde as a chromogenic reagent" Journal of the Chemical Society of Pakistan, vol. 18, No. 1, pp. 8–11, 1996.

Dai Fang et al.: "Update and evaluation of the effectiveness of different thiols and micellar media in Roth's Fluorimetric Method for the determination of primary amino acid compounds" Microchemical Journal, vol. 57, No. 2, pp. 166–198 10/97.

* cited by examiner

POLYMER FOR BINDING AMINE CONTAINING LIGANDS AND USES THEREOF

TECHNICAL FIELD

The present invention relates to a polymer capable of binding amine ligands, to its preparation, and to uses including assays and chromatography.

There is an ever-increasing need for the measurement and quantification of mankind's activities. Sensors are partially fulfilling this requirement though sensors for many applications are not readily available in a form suitable for commercialisation.

One particular class of sensors, that is bio- and chemo-recognition sensors, requires the integration of ligands (recognition elements) to a transducer. The integration should normally enable changes in the recognition element caused by interaction with a corresponding analyte to be converted into a measurable signal via the transducer.

The immobilisation of the ligands to the surface of a suitable transducer is a necessary step in sensor manufacturing. Desirable properties of this process include: placement of appropriate amounts of ligands on detector surface using simple procedures, maintenance of biorecognition activity of the ligands after immobilisation, and minimisation of non-specific interactions between the sample and the recognition element or other parts of the sensor.

BACKGROUND ART

Recently a wide variety of methods have been discovered for attaching different ligands to transducers in order to create effective and sensitive bio- and chemosensors.

Examples are disclosed in U.S. Pat. No. 4177038, U.S. Pat. No. 4250267, U.S. Pat. No. 4784962, U.S. Pat. No. 5242828, U.S. Pat. No. 5436161 and Löfås, S., Johnsson, B., Tegendal, K., Rönnberg, I., "Dextran modified gold surfaces for surface plasmon resonance sensors: immunoreactivity of immobilised antibodies and antibody-surface interaction studies", (1993), Colloids and Surfaces B: Biointerfaces, 1: 83–89.

Also of interest is Simons, S., Jr. et al. "Reaction of O-Phthalaldehyde and Thiols With Primary Amines; Formation of 1-Alkyl (and Aryl) Thio-.alpha.-Akylisoindoles", (1978), J. Org. Chem., 43 (14): 2886–2896.

A common approach is the use of transducer surfaces modified with hydrogel layers (U.S. Pat. No. 5436161), such as carboxymethyl-dextran. Typically, hydrogel polymers are covalently immobilized to a transducer surface to form a thin hydrogel layer. Ligands can be covalently immobilised to the hydrogel polymer using a chemical activation. Such multi-step process places a significant overhead cost on any mass-manufacture of a sensor device. An alternative approach, which can eliminate this disadvantage, would be of considerable benefit.

DISCLOSURE OF INVENTION

In a first aspect the invention provides a method of immobilising an amino-group containing ligand L—NH$_2$ by means of a dialdehyde component OHC—X—CHO and a polymerisable component R—Z wherein R is a polymerisable moiety and Z is selected from —SH, —S-alkyl, —CN and —SO$_2$ by carrying out the following reactions simultaneously and/or sequentially in any chemically feasible order:

i) polymerisation of the polymerisable moieties R, optionally together with one or more comonomers;

ii) reaction of a component containing —Z with the dialdehyde component;

iii) reaction of L—NH$_2$ with the dialdehyde component or with the product of reaction (ii).

The dialdehyde component is preferably a 1,4-dialdehyde, generally conjugated

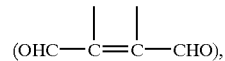

generally forming part of an aromatic ring system, e.g. it may be o-phthaldialdehyde (I):

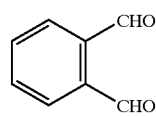

Conjugation may be desirable to give a product detectable by optical methods, e.g. involving fluorescence.

The polymerisable moiety R generally contains one or more carbon-carbon multiple bonds. For example, R—Z may be allyl mercaptan.

Polymerisation may involve comonomers as well as the R moieties. They can be used to 'dilute' the Z groups in the polymer. Particularly when Z is —SH, such dilution may be desirable to reduce the occurrence of cross-linking through Z—Z (e.g. disulphide) bridges. Comonomers can also be used to regulate polymer solubility, to suit particular applications.

Particularly when Z is —SH or —S-alkyl, the reaction may be suitable for achieving self-assembly of a polymer on a suitable surface (particularly a metal surface (especially noble metal) or a surface having —SH groups). Thus a preferred class of embodiment is based on the ability of a synthetic polymer, containing thioacetal groups formed by a mercapto group and phthalic dialdehyde to self-assemble on a metal surface and bind amino containing ligands to form a fluorescent complex. The polymer can be synthesised using ion, radical polymerisation or polycondensation. It is preferable that at least one of the monomers used for polymerisation contains free SH groups. In another variant polymer can be first produced using an SH-group containing monomer and subsequently treated with dialdehyde to form a thioacetal. IL is also possible to use CN and SO$_2$-containing monomers instead or simultaneously with SH-containing monomer for the polymer preparation.

Surfaces coated with a polymer of the invention may be microtitre plates, wells, transducers (e.g. for surface plasmon resonance or electrochemical devices), or binding materials e.g. for chromatography.

A polymer of the invention may comprise units of formula II:

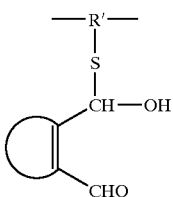
(II)

where R' is derived from polymerisation of an R group. The unit

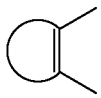

is preferably provided by an aromatic ring system, e.g. being

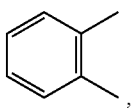

optionally substituted and/or fused to form a polycycle. A polymer of the invention incorporating L—NH$_2$ may comprise units of formula III:

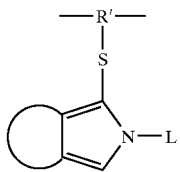

where

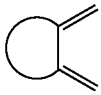

corresponds to

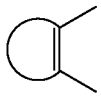

in formula II, e.g. being

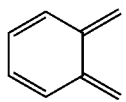

(optionally substituted and/or fused.

The polymers described above can be used in affinity chromatography or sensors. Such a polymer containing SH groups may adsorb on a metal or SH-containing surface (e.g. during the synthesis) forming a homogeneous, stable coating. It is possible to make first a surface coating with a polymer of RSH, with following treatment of this polymer using dialdehyde, preferably phthalic dialdehyde and next amino-containing ligand. Again, ligand can be immobilised by simultaneous addition of the desired compound with dialdehyde to the SH-containing polymer. Species, such as cells, enzymes, viruses, fungi, antibodies, proteins, peptides, amino acids, nucleic acids and derivatives or mixtures can be easily immobilised on the polymer, synthesised as described above. The immobilised species may itself serve for binding a second type of ligand. Binding the second type of ligand may affect measurable properties, e.g. fluorescence, so that the binding may be detected. The ligands of first and second type may constitute specific binding pairs, e.g. antibody-antigen.

Ligand immobilisation on the polymer surface includes one-step interaction between thioacetal and amino group without chemical activation of the polymer or ligand functional groups. Formation of fluorescent complexes can be used to monitor binding. The isoindole complex formed by thioacetal with ligand amino groups was found to be very stable, which permits the use of strong acidic conditions for surface regeneration.

The homologous aromatic dialdehyde, o-phthaldialdehyde, or thioacetal is essentially nonfluorescent until reacted with primary amine in the presence of excess cyanide or mercaptan to yield a fluorescent isoindole. Monitoring of the polymer fluorescence provides an opportunity to directly control the amount of the bound substances to the polymer surface, which can be further used in sensors and assays.

MODES FOR CARRYING OUT THE INVENTION

Figure 1:
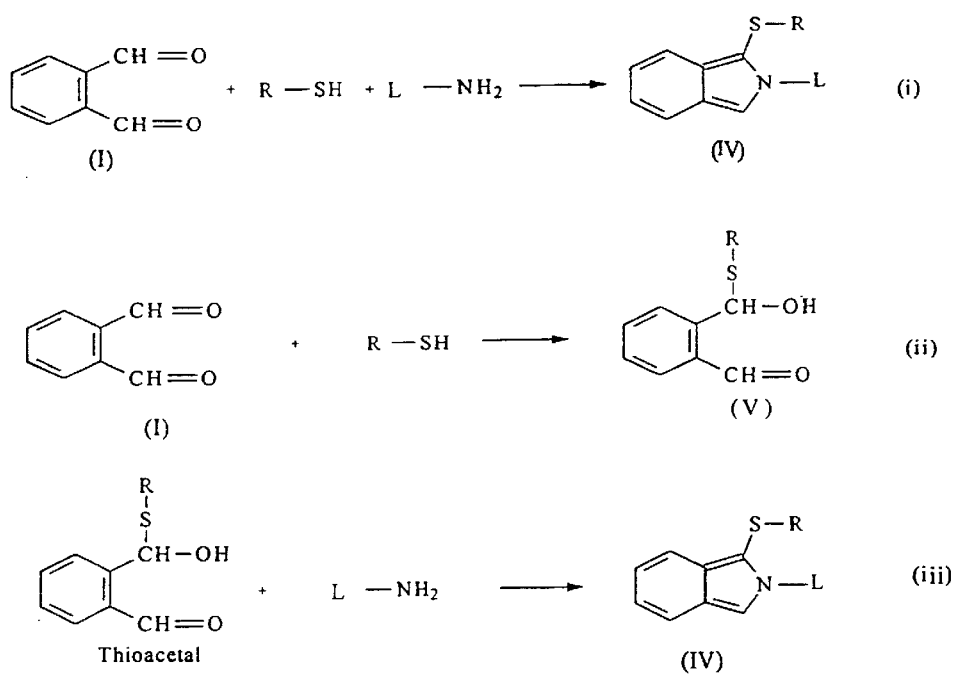
FIG. 1 shows possible reaction schemes usable in the invention.

FIG. 1 shows some examples of reaction types that may be used in the invention.

Reaction (i) shows the interaction of o-phthaldialdehyde ("OPA"), (I) with a polymerisable thiol R—SH and an amine ligand L—NH$_2$ to produce a fluorescent isoindole (IV).

Reactions (ii) and (iii) show this process carried out in sequential stages: reaction of OPA (I) with the thiol to form a thioacetal (V), which subsequently reacts with the amine ligand.

The preparation of a polymer embodying the invention and some experiments carried out with it will now be described.

1. Preparation of the Polymer 134 mg of OPA and 82 mg of allyl mercaptan (AM) were dissolved in 2 ml of (2-hydroxyethyl)methacrylate and 2 ml of acetonitrile. 50 mg AIBIN was used as a catalyst for this reaction. Reaction mixture was incubated overnight at 80°. Polymer (OPA-AM) was dissolved in ethanol and 0.1 M sodium phosphate buffer pH 8.0 was added. The resulting pellet was collected and washed with water using glass filter.

2. Fluorometry With Reactive Polymer 30 mg of OPA-AM polymer was dissolved in 10 ml of acetonitrile/$H_2O$ (1:1). To adjust mixture for basic pH 30 ml 4% NaOH was added. Fluorescence measurements were performed with RF-5301 PC Spectrofluorophotometer (Shimadzu, Japan).

Figure 2:
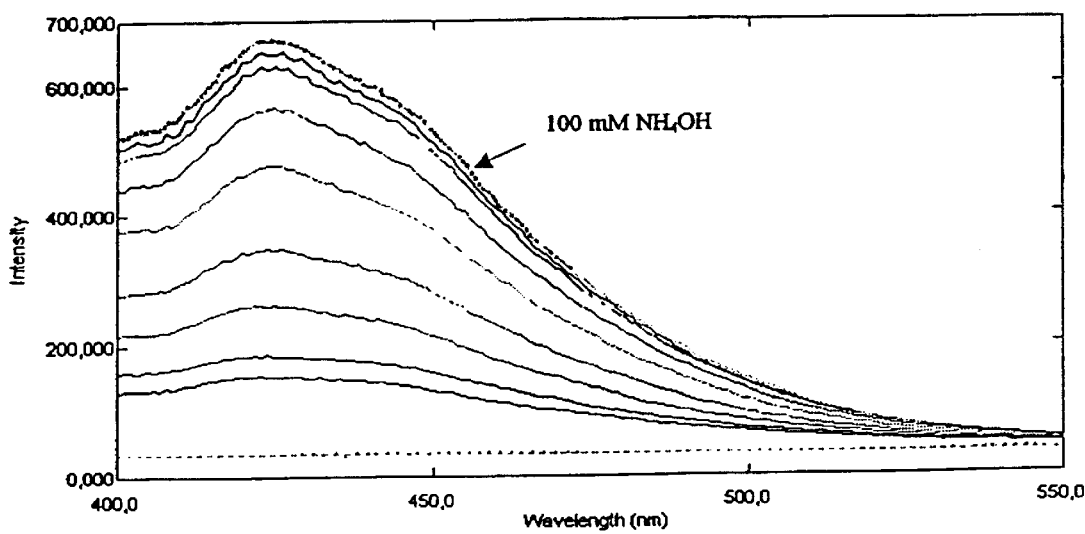
FIG. 2 depicts a dependance of the OPA-AM-polymer emission spectra for different ammonium hydroxide concentrations (1–100 mM). Dotted line- control without ammonium hydroxide. Reaction mixture is 3 mg/ml polymer in 1:1 mixture of acetonitrile and 0.1 M phosphate buffer, pH 7.8. Incubation time is 30 min.
Figure 3:
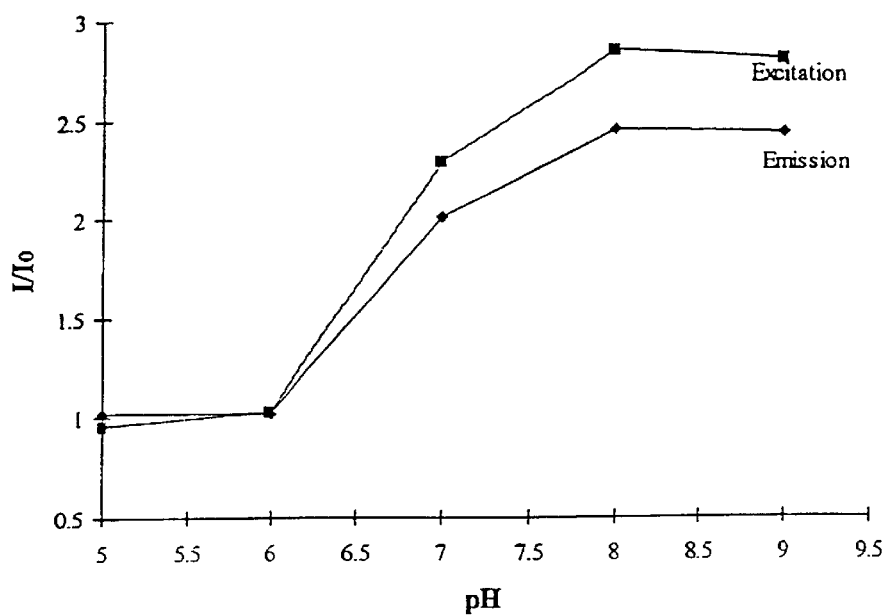
FIG. 3 depicts a dependence of OPA-AM-polymer response for 100 mM ammonia on pH.

The polymer was excited at wavelength 355 nm and emission spectrum was measured. It was found that fluorescence intensity depends on the presence of amino-groups in the sample (see FIG. 2), incubation time (not shown) and pH (see FIG. 3).

Figure 4:
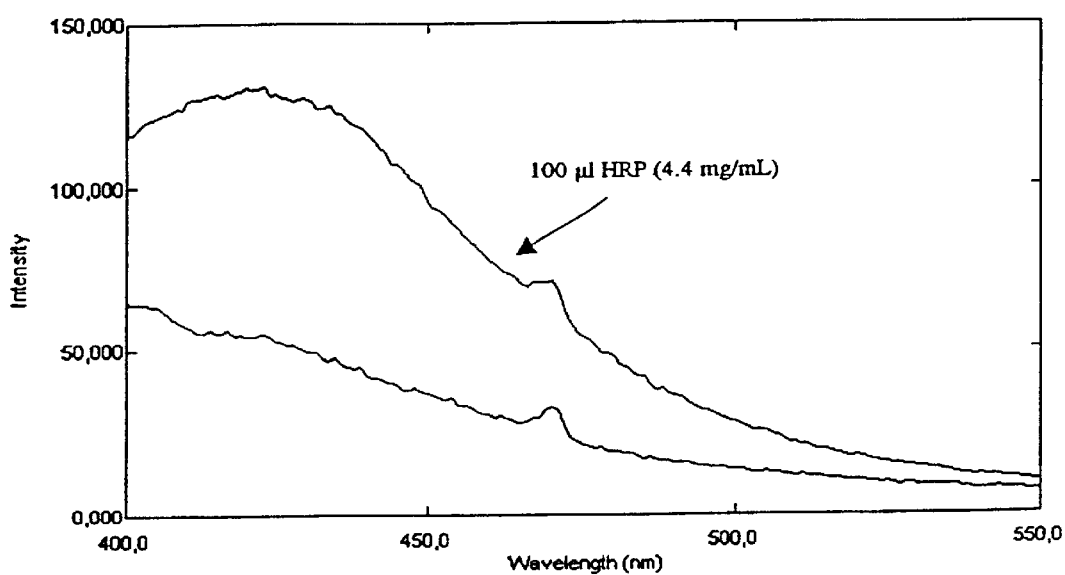
FIG. 4 depicts a change in the emission spectra intensity of the OPA-AM-polymer (1(lamda)$_{exc}$ 355 nm) as response to the addition of horseradish peroxidase.

The same experiments were carried out using horseradish peroxidase giving similar results (FIG. 4.).

3. Application of OPA-AM Polymer for Ligand Immobilisation in Surface Plasmon Resonance Glass prisms coated with >>50 nm gold layer were immersed in the polymer solution in methanol (1 mg/ml) for 5 min, washed twice with methanol and water.

Figure 5:
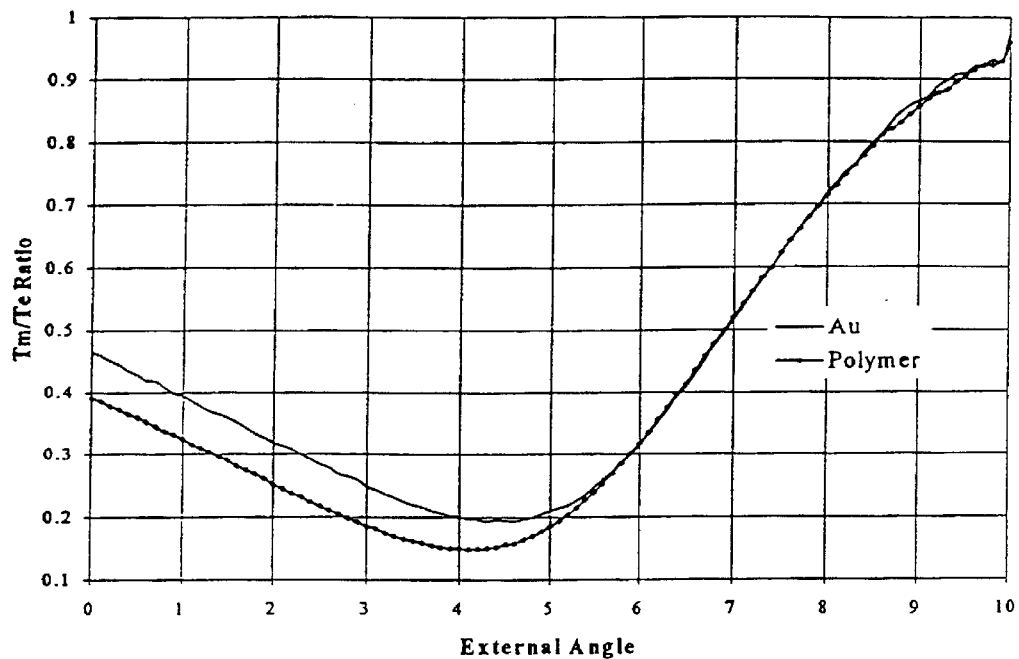
FIG. 5 depicts a polymer deposition on gold surface using flow system.

In another variation of the method the polymer solution in methanol was run through the flow cell (20 ml volume) with flow rate 5 ml/min for 10 min. Methanol was then run for 10 min to remove excess polymer. The shift in position of reflective curve minimum ($A_{SPR}$) is a result of polymer immobilisation (FIG. 5).

100 ml human IgG solution (0.1 mg/ml, 100 mM sodium borate buffer, pH 9.0) was injected and rate of immobilisation was measured using angle scanning. The displacement of the reflective curve minimum position was measured.

Figure 6:
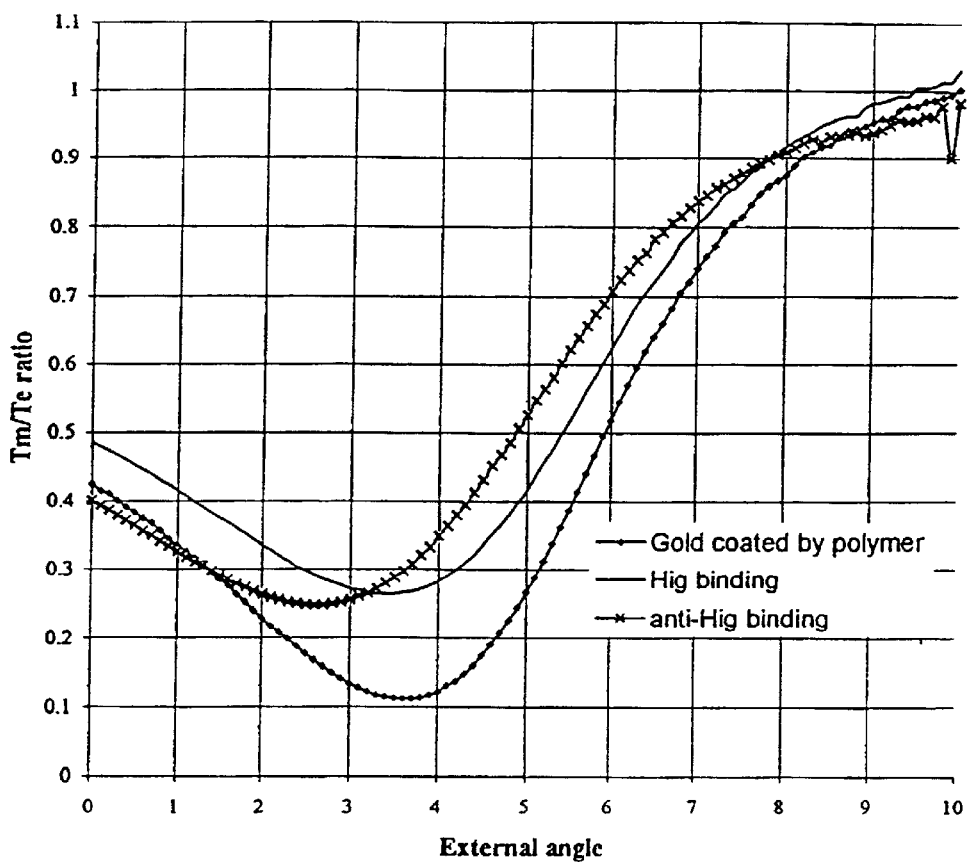
FIG. 6 depicts a covalent binding of human immunoglobulin to the OPA-AM-polymer coated surface followed by anti-human immunoglobulin binding.
Figure 7:
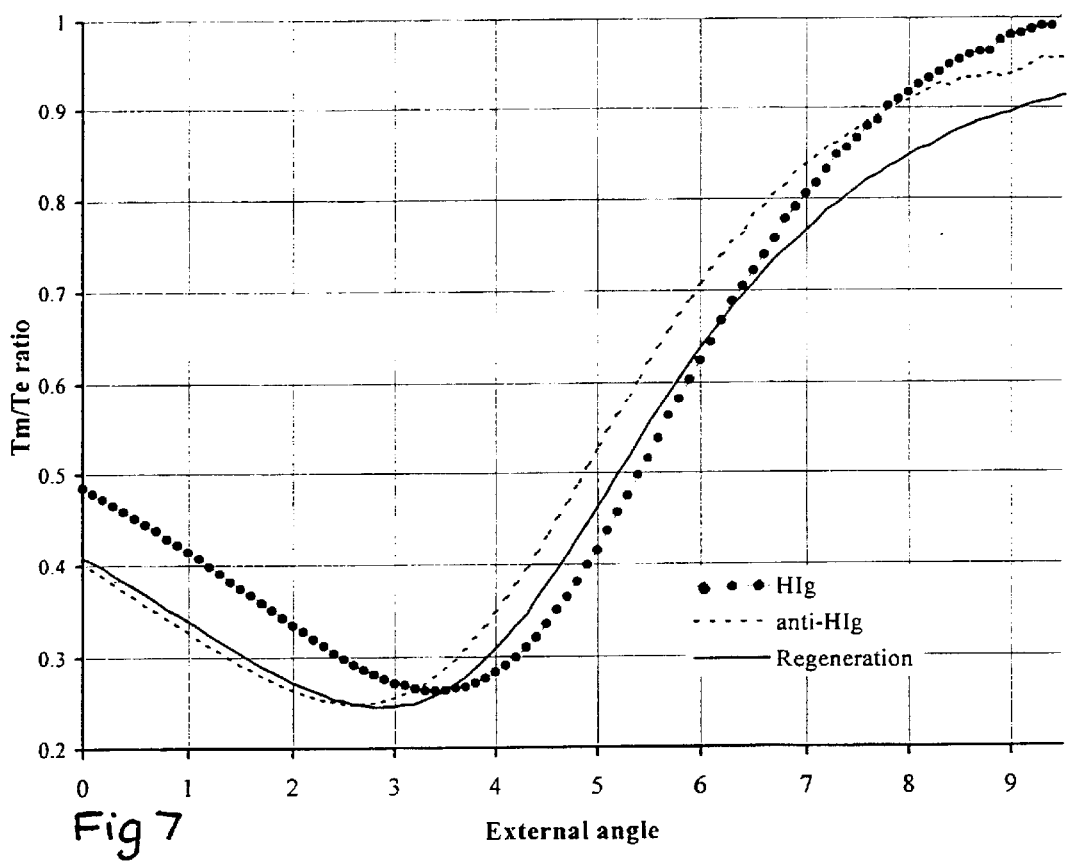
FIG. 7 depicts a regeneration of surface coated with polymer with 0.1% SDS/10 mM HCl.

The adsorption of the second antibodies specific for covalently immobilised HIGg (anti-HIGg) was observed (FIG. 6). The surface was regenerated with mixture of 0.1% SDS/10 mM HCl (FIG. 7).

Figure 8:
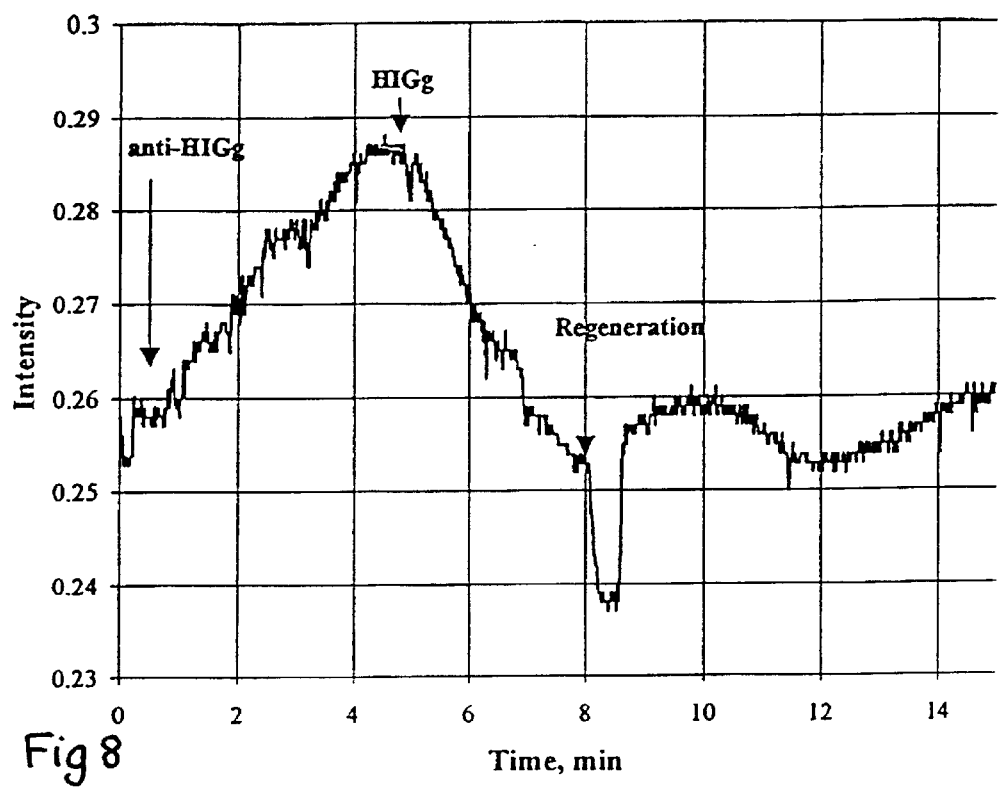
FIG. 8 depicts a displacement of anti- human immunoglogulin (HIGg) by the human immunoglobulin from the prism surface coated by OPA-AM-polymer with following regeneration. Concentrations of HIGg and anti-HIGg-10 mg/ml.
Figure 9:
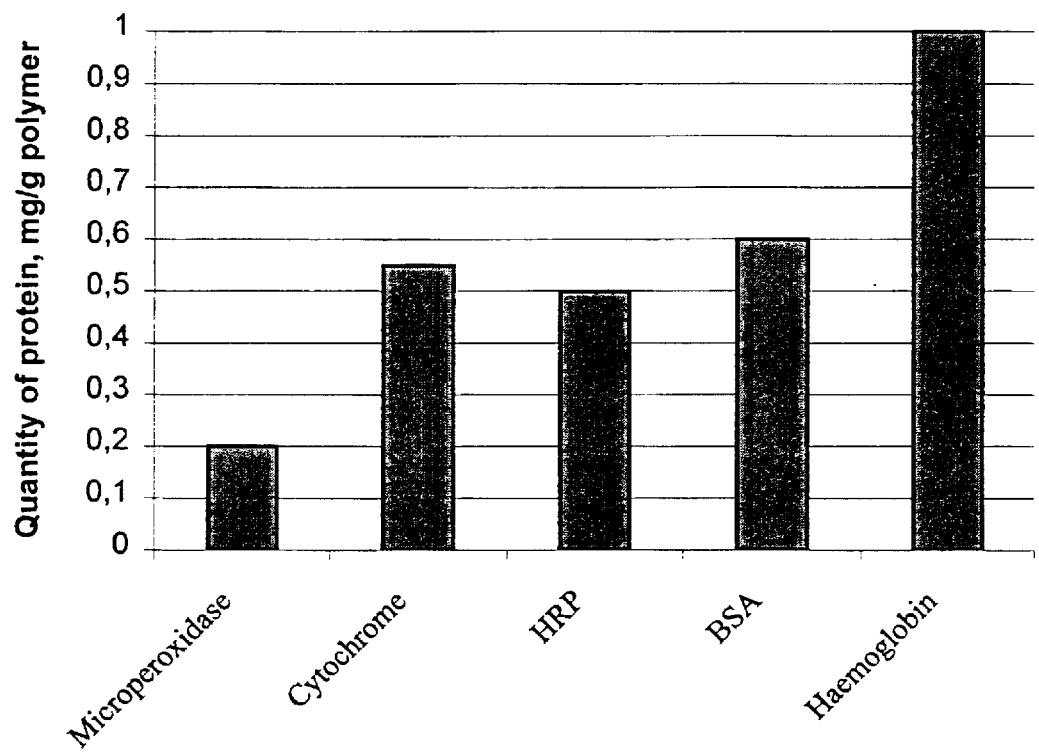
FIG. 9 is a bar chart showing the binding capacity of the OPA-AM polymer for different proteins.

The time scanning was applied to measure binding/displacement events (FIG. 8). It was found that OPA-AM matrix creates reactive surface, which is suitable for optic transducers. It is stable upon storage, simple to prepare and is suitable for mass-production of biosensor devices.

Protein immobilization. The binding capacity of the polymer was demonstrated with several proteins: microperoxidase (FW=1 kD), cytochrome C (FW=12.4 kD), horseradish peroxidase (HRP) (FW=44 kD), bovine serum albumin (BSA) (FW=66 kD) and haemoglobin (FW=67 kD). 10 mg of polymer was incubated with 400 ml of protein solution (5 mg/ml) in 10 mM HEPES buffer, pH 8.6 for 18 hours. The protein concentration before and after sorption was measured spectrophotometrically using a BCA method [cf Osnes T, Sandstad O, Skar V, Osnes M, Kierulf P, Scandinavian journal of clinical & laboratory investigation 1993; 53 (7): 757–763.] and calculated using calibration curves obtained individually for each protein. It was calculated that 1 g of the polymer can bind 0.6 mg of the BSA, 0.55 mg cytochrome C, 0.2 mg microperoxidase, 0,5 mg horseradish peroxidase and 1 mg haemoglobin (Figure). The binding capacity of the polymer and sensitivity of the fluorescent detection therefore depend on the number of amines available—a function of both the protein's structure and its amino acid composition. The immobilisation rate was found comparable with commercial sorbents used for protein immobilisation like activated CN Sepharose 4B (Pharmacia, Sweden). It is anticipated that the polymer can be used as effective alternative immobilisation matrix in affinity chromatography for immobilisation of low-weight organic amines, proteins and nucleic acids as well as sensor/assay components for primary amines detection.

What is claimed is:

1. A polymer comprising units of the formula

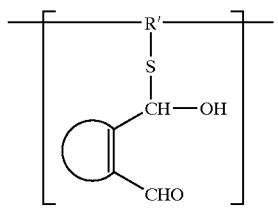

wherein R' is derived form a polymerizable moiety containing one or more carbon-carbon multiple bonds.

2. The polymer according to claim 1 wherein

is an aromatic ring system.

3. A binding medium comprising a carrier material having a surface which bears a polymer according to claim 1.

4. The binding medium according to claim 3 which is a stationary phase for chromatography.

5. A chromatography column or plate having a stationary phase according to claim 4.

6. A biosensor device having a surface covered with the binding medium as claimed in claim 3.

7. A method of assaying a sample for ligands, comprising:
exposing the surface of the device of claim 3 bearing said binding medium to a sample suspected of containing said ligands; and
monitoring optical properties of said binding medium.

8. The method according to claim 7, wherein the carrier material bears a polymer comprising units of the formula

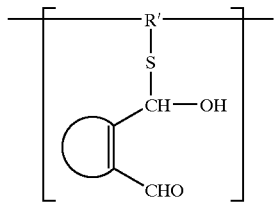

where R' is derived from a polymerizable moiety containing one or more carbon-carbon multiple bonds and said polymer serves for binding amino-group containing ligands.

9. The binding medium according to claim 3, wherein the carrier material bears a polymer comprising units of the formula

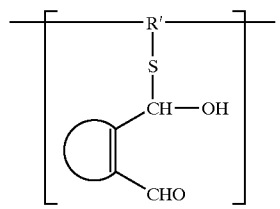

where R' is derived from a polymerizable moiety containing one or more carbon-carbon multiple bonds and said polymer serves for binding amino-group containing ligands.

10. A polymer comprising units of the formula

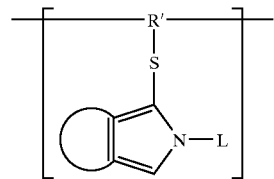

wherein R' is derived form a polymerizable moiety containing one or more carbon-carbon multiple bonds and

is derived from a ligand L—NH$_2$ which is selected from the group consisting of an amino acid, peptide, protein, nucleic acid and derivatives thereof.

11. A polymer according to claim 10 wherein

is an aromatic ring system.

12. A binding medium comprising a carrier material having a surface which bears a polymer according to claim 10.

13. A binding medium according to claim 12, which is a stationary phase for chromatography.

14. A chromatography column or plate having a stationary phase according to claim 13.

15. A method of immobilizing an amino-group containing ligand L—NH$_2$, comprising:
    polymerizing a monomer R—Z, wherein R is a polymerizable moiety and Z is a functional group selected from the group consisting of —SH, —S-alkyl, —CN and —SO$_2$, optionally in the presence of a comonomer;
    reacting a dialdehyde component of the formula OHC—X—CHO, wherein X is a linking group, with said functional group; and then
    reacting a ligand L—NH$_2$ with the dialdehyde modified polymer.

16. The method of claim 15, wherein the dialdehyde component is a 1,4-dialdehyde.

17. The method of claim 15, wherein the dialdehyde component is of the form:

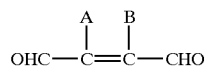

wherein the partial structure A—C=C—B defines an aromatic ring system.

18. The method of claim 17, wherein the dialdehyde component is o-phthaldialdehyde.

19. The method according to claim 15, wherein R contains one or more carbon-carbon double or triple bonds.

20. The method according to claim 15, wherein said polymerizable component is a thiol R—SH.

21. A method of immobilizing an amino-group containing ligand L—NH$_2$, comprising:
    reacting a ligand L—NH$_2$ and a dialdehyde component of the formula OHC—X—CHO, wherein X is a linking group, in the presence of a polymerizable monomer R—Z, wherein R is a polymerizable moiety and Z is a functional group selected from the group consisting of —SH, —S-alkyl, —CN and —SO$_2$, optionally in the presence of a comonomer, thereby effectively polymerizing the monomer and optional comonomer and simultaneously reacting the ligand L—NH$_2$ with the dialdehyde to form a product which reacts with the functional group Z of the polymerizing monomer R—Z.

22. The method of claim 21, wherein the dialdehyde component is a 1,4-dialdehyde.

23. The method of claim 21, wherein the dialdehyde component is of the form:

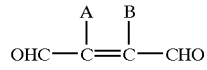

wherein the partial structure A—C=C—B defines an aromatic ring system.

24. The method of claim 23, wherein the dialdehyde component is o-phthaldialdehyde.

25. The method according to claim 21, wherein R contains one or more carbon-carbon double or triple bonds.

26. The method according to claim 21, wherein said polymerizable component is a thiol R—SH.

27. A method of immobilizing an amino-group containing ligand L—NH$_2$, comprising:
    reacting a ligand L—NH$_2$ and a dialdehyde component of the formula OHC—X—CHO, wherein X is a linking group, thereby forming a reaction product; and then
    reacting the reaction product, which reacts with the functional group Z of polymerizable monomer R—Z, with (1) a polymer prepared by polymerizing a monomer R—Z and optionally with a copolymerizable comonomer or with (2) a monomer R—Z and optionally with a copolymerizable comonomer, followed by polymerization of the monomer material, wherein R is a polymerizable moiety and Z is a functional group selected from the group consisting of —SH, —S-alkyl, —CN and —SO$_2$.

28. The method of claim 27, wherein the dialdehyde component is a 1,4-dialdehyde.

29. The method of claim 27, wherein the dialdehyde component is of the form:

wherein the partial structure A—C=C—B defines an aromatic ring system.

30. The method of claim 27, wherein the dialdehyde component is o-phthaldialdehyde.

31. The method according to claim 27, wherein R contains one or more carbon-carbon double or triple bonds.

32. The method according to claim 27, wherein said polymerizable component is a thiol R—SH.

33. A method of immobilizing a ligand on a surface, comprising:

adsorbing a polymer prepared by polymerizing a monomer of the formula R—SH, optionally in the presence of a comonomer, on a metal surface;

reacting a dialdehyde of the formula OHC—X—CHO, wherein X is a linking group, with the surface adsorbed polymer; and then reacting a ligand L—$NH_2$ with the reacted polymer, thereby immobilizing the ligand on the surface.

34. The method according to claim 33, wherein the immobilized ligand fluoresces which is detected by a fluorescent light detecting device.

35. A method of immobilizing a ligand on a surface, comprising:

adsorbing a monomer of the formula R—SH, optionally in the presence of a comonomer, on a metal surface with the presence of a dialdehyde of the formula OHC—X—CHO, wherein X is a linking group, and then effecting polymerization of the (co)monomer and reaction of the dialdehyde with the —SH functional groups of the polymer; and then reacting a ligand L—$NH_2$ with the reacted polymer, thereby immobilizing the ligand on the surface.

36. The method according to claim 35, wherein the immobilized ligand fluoresces which is detected by a fluorescent light detecting device.

\* \* \* \* \*